United States Patent [19]

Lion et al.

[11] Patent Number: 5,650,159
[45] Date of Patent: Jul. 22, 1997

[54] COSMETIC OR PHARMACEUTICAL COMPOSITION COMPRISING AN AQUEOUS DISPERSION OF POLYMER

[75] Inventors: Bertrand Lion, Livry Gargan; Jean Mondet, Aulnay Sous Bois; Colette Cazeneuve, Paris, all of France

[73] Assignee: L'Oréal, Paris, France

[21] Appl. No.: 477,945

[22] Filed: Jun. 7, 1995

[30] Foreign Application Priority Data

Jun. 8, 1994 [FR] France ................... 94 07017

[51] Int. Cl.$^6$ ........................................ A61K 6/00
[52] U.S. Cl. ............... 424/401; 424/61; 424/70.7; 424/70.9; 424/70.11; 424/70.12
[58] Field of Search .................. 424/401, 70.7, 424/70.9, 70.11, 70.12, 61

[56] References Cited

U.S. PATENT DOCUMENTS

| | | | |
|---|---|---|---|
| 4,198,330 | 4/1980 | Kaizerman et al. | 525/185 |
| 4,300,580 | 11/1981 | O'Neill et al. | 132/7 |
| 4,946,932 | 8/1990 | Jenkins | 528/272 |
| 4,985,239 | 1/1991 | Yahagi et al. | 424/70.12 |
| 5,089,250 | 2/1992 | Forestier et al. | 424/401 |
| 5,254,542 | 10/1993 | Sakuta et al. | 514/63 |
| 5,475,126 | 12/1995 | Yoshida et al. | 424/401 |

FOREIGN PATENT DOCUMENTS

| | | |
|---|---|---|
| 0 297 576 | 1/1989 | European Pat. Off. . |
| 0 309 114 | 3/1989 | European Pat. Off. . |
| 0 353 896 | 2/1990 | European Pat. Off. . |
| 0 478 284 | 4/1992 | European Pat. Off. . |
| 2 680 684 | 3/1993 | France . |
| 2 238 242 | 5/1991 | United Kingdom . |

OTHER PUBLICATIONS

Research Disclosure, "Hair Grooming Compositions", vol. 326, (1991) New York (USA), pp. 390–391.
Research Disclosure, "Fast Drying Aqueous Nail Polish", vol. 326, (1991) New York (USA), p. 395.

*Primary Examiner*—Mark D. Sweet
*Attorney, Agent, or Firm*—Finnegan, Henderson, Farabow, Garrett & Dunner, L.L.P.

[57] ABSTRACT

The present invention relates to a cosmetic or pharmaceutical composition comprising an aqueous dispersion of polymers, in particular as film-forming agent. The said aqueous dispersions are obtained by radical polymerization of radical monomer, within and/or partially at the surface, of preexisting particles of at least one polymer chosen from the group consisting of polyurethanes and/or polyureas.

23 Claims, No Drawings

COSMETIC OR PHARMACEUTICAL COMPOSITION COMPRISING AN AQUEOUS DISPERSION OF POLYMER

The present invention relates to a cosmetic or pharmaceutical composition comprising an aqueous dispersion of polymers, as well as the use of the said dispersion as film-forming agent in a cosmetic or pharmaceutical composition.

It is known to use aqueous dispersions of polymers in cosmetic or pharmaceutical compositions. These dispersions are generally used as film-forming agents, in particular for make-up products such as nail varnishes and hair products.

It is known, for example by Patent Application EP 418,469, which is herein incorporated by reference in its entirety, to employ an aqueous dispersion of polyurethane, alone or in combination with an aqueous dispersion of vinyl and/or acrylic esters, in nail varnishes. Polyurethanes in aqueous dispersion are also described in Applications EP 391,322 and EP 214,626, each of which is incorporated by reference in its entirety, either for an application in nail varnishes or for a hair application.

The properties of the aqueous dispersions thus obtained depend upon the nature of the polymers, and thus of the monomers, from which they are prepared. It may, however, be advantageous to be able to modify these properties slightly, for example by accentuating/optimizing a particularly advantageous property, or by developing a new property which the said dispersion could not have on account of the nature of the polymer which it comprises.

The object of the invention is to propose a composition comprising an aqueous dispersion of a polymer chosen from the group consisting of polyurethanes and polyureas, which has enhanced properties when compared with the dispersions of polyurethane and/or of polyurea of the prior art.

One object of the invention is thus a cosmetic or pharmaceutical composition comprising an aqueous dispersion of polymer consisting of particles resulting from the radical polymerization of at least one radical monomer, within and/or partially at the surface, of preexisting particles of at least one polymer chosen from the group consisting of polyurethanes and/or polyureas.

Another object of the invention is the use of such a dispersion in a cosmetic or pharmaceutical composition, as film-forming agent.

In the rest of the present description, the term "polyurethane" refers to any polymer, alone or as a mixture, chosen from the group consisting of polyurethanes and polyureas.

It has been observed that the compositions according to the invention, comprising aqueous dispersions of polyurethane hybrid polymers, have particular properties which are not possible to obtain using, for example, a simple mixture of preexisting aqueous dispersions of polyurethane and of acrylic and/or vinyl polymers.

Another advantage of the present invention is, starting with an already-existing aqueous dispersion of polymer, to be able to develop and/or optimize certain particularly advantageous properties, in a relatively controlled manner.

In order to prepare the composition according to the invention, an aqueous dispersion of polyurethane is first of all prepared.

This dispersion may be prepared by a person skilled in the art based on his general technical knowledge, in particular in the following way.

The water-insoluble polyurethane polymer is dissolved in an organic solvent that is sparingly soluble in water, water is added to this solution and it is mixed so as to form an emulsion, followed by evaporation of the organic solvent so as to obtain an aqueous dispersion of the polyurethane polymer in water, having a solids content of about 30–50% by weight.

The aqueous dispersion of "polyurethane" used may be an aqueous dispersion of anionic, cationic or amphoteric polyurethane, of polyester-polyurethane, of polyether-polyurethane and/or of polyurea, alone or as a mixture.

The said polyurethane may, for example, be an aliphatic, cycloaliphatic or aromatic polyurethane, polyurea/urethane or polyurea copolymer, containing, alone or as a mixture,

- at least one sequence of linear or branched aliphatic and/or cycloaliphatic and/or aromatic polyester origin, and/or
- at least one sequence of aliphatic and/or cycloaliphatic and/or aromatic polyether origin, and/or
- at least one branched or unbranched, substituted or unsubstituted silicone-containing sequence, for example polydimethylsiloxane or polymethylphenylsiloxane, and/or
- at least one sequence containing fluorinated groups.

The polyurethanes as defined in the invention may also be obtained from branched or unbranched polyesters, or from alkyds containing labile hydrogens which are modified by reaction with a diisocyanate and a difunctional organic compound (for example dihydro, diamino or hydroxyamino), and also containing either a carboxylate or carboxylic acid group, or a sulphonate or sulphonic acid group, or a neutralizable tertiary amine group or a quaternary ammonium group.

The aqueous dispersion of polyurethane hybrid polymers according to the invention is obtained by radical polymerization of at least one monomer within and/or partially at the surface of preexisting particles of polyurethane.

The radical monomer may be of vinyl or acrylic nature, and may be anionic, cationic, nonionic or amphoteric. It is also possible to use a mixture of monomers of different nature. The monomer, or the mixture of monomers, is preferably insoluble or sparingly soluble in water. Among the monomers which may be employed, there may be mentioned esters of acrylic or methacrylic acid, such as methyl, ethyl, propyl, butyl, isobutyl, tert-butyl and 2-ethylhexyl acrylate or methacrylate; N-substituted or N,N-substituted acrylamides or methacrylamides; vinyl esters such as vinyl acetate; styrene.

It is also possible to use, alone or as a mixture, a vinyl, acrylic or methacrylic monomer containing one or more siloxane groups, in particular

- the monomer of formula $CH_2=C(CH_3)-C(O)-O-(CH_2)_3-Si-[O-Si(CH_3)_3]_3$
- a silicone-containing macromonomer containing a vinyl, allyl, ester ether or acrylamide or methacrylamide monofunctional end group, of formula $CH_2=C(R1)-C(O)-X-(CH_2)_p-[Si(CH_3)(R4)-O-]_n-Si(CH_3)_2-R3$ in which R1 represents H or $CH_3$, X represents O or NH, p is an integer which may be zero, R3 and R4 independently represent $CH_3$ or an aliphatic, cycloaliphatic or aromatic group, and n is an integer, preferably ranging from 3–300.

It is also possible to use a vinyl, allyl, ester ether or acrylamide or methacrylamide monomer containing one or more halogenated groups, in particular chlorinated and/or fluorinated groups, and/or containing a group absorbing in the UVA and/or UVB region and which may provide sun protection after polymerization, in particular benzylidenecamphor and benzotriazole groups, which may or may not be substituted, among which there may be mentioned 2-(2'-hydroxy-5-methacrylyloxyethylphenyl)-2-H-benzotriazole.

When the monomer, or the mixture of monomers, is in liquid form at room temperature, the radical polymerization may be carried out without using solvent.

When the monomer, or the mixture of monomers, is in solid form at room temperature, it may be dissolved before the polymerization, preferably in an organic solvent, for example one which is polar and water-miscible, such as methanol. In this case, after polymerization, the organic solvent contained in the polymer dispersion may, if necessary, be distilled off.

The aqueous dispersions according to the invention are prepared under conditions such that the monomer polymerizes within and/or partially at the surface of the polymer particles in the absence of any nucleation, that is to say without there being any formation of new particles.

To do this, the polyurethane polymer may be introduced as an aqueous dispersion having a solids content of 30–50% by weight into a polymerization reactor. The monomer, or the mixture of monomers, may then be added thereto, as it is or dissolved in a suitable solvent, as may a radical polymerization initiator.

Depending on its nature, the radical initiator is introduced either in solution form in an organic solvent, or in aqueous solution form, or dissolved in the mixture of monomers.

In the first case, it may be added at the same time as the dissolved monomer, and in the second case, it may be added after the monomer.

It is possible to use a water-insoluble organic radical polymerization initiator of peroxide or percarbonate type, such as tert-butylperoxy-2-ethylhexanoate, or a water-soluble organic initiator, or an inorganic initiator such as potassium persulphate.

Thus, the mixture comprising the polyurethane polymer, the monomer or the mixture of monomers and the polymerization initiator is prepared.

This mixture is then heated to the temperature necessary to allow the initiator to decompose and the polymerization is continued until the monomers have been exhausted.

It should be noted that the polymerization may thus be carried out in the absence of a surfactant in the polyurethane dispersion.

An aqueous dispersion of polyurethane hybrid polymer is thus obtained. The particles constituting this final dispersion are in the form of composite particles, similar to an "alloy" of the two base polymers and comparable in size to that of the polyurethane particles before radical polymerization.

The dispersions thus obtained have their own intrinsic properties, which are different from those which would be obtained by mixing two aqueous dispersions of each of the constituents.

The dispersions according to the invention may be used as film-forming agent in cosmetic or pharmaceutical compositions, in the same way as an aqueous dispersion of polymer according to the state of the art.

It is possible, for example, to use the dispersions according to the invention as film-forming agent in hair products such as fixing hairsprays or shampoos, styling lotions or mousses, in make-up products such as nail varnishes or mascaras, or alternatively in care bases for nails or skin care products.

The dispersions according to the invention may also be used in products intended for the photoprotection of the skin and/or the hair against ultraviolet radiation, in particular against solar radiation, when they contain a suitable monomer, capable of providing a certain level of sun protection.

The invention is illustrated in greater detail in the examples which follow, in which the percentages are given by weight. The hardness is measured using a Persoz pendulum, at a temperature of 30° C. and a relative humidity (RH) of 50%.

EXAMPLE 1

195.5 g of aqueous dispersion of polyester-polyurethane containing carboxylic groups (solids content: 35.8%), sold under the name SANCUR 815 by Sancor, were introduced into a reactor preheated to approximately 90° C.

224.6 ml of deionized water were added and the mixture was left stirring under a nitrogen sparge, at about 80° C. for 15 minutes.

30 g of methyl methacrylate were then added dropwise, which took about 45 minutes, and the mixture was then left to stir for 1 hour at 80° C.

0.5 ml of tert-butylperoxy-2-ethyl hexanoate (Trigonox 21S from Akzo) was added and the mixture was left to react for 6 hours, with stirring and under a nitrogen sparge, at 80° C.

The mixture then obtained had the same appearance as at the start, although all of the monomer had polymerized.

The temperature of the reaction mixture was reduced to 25° C. and the dispersion was concentrated under reduced pressure until a solids content of 40% was obtained.

A dispersion was thus obtained which, after filtration on nylon cloth, had the following characteristics:

mean particle size determined by a quasi-elastic light-scattering apparatus of the type Coulter N4, from Coultronix: 36 nm polydispersity: 0.2

Given that the size of the particles in the initial polyurethane dispersion (SANCUR 815) was 31 nm with a polydispersity of 0.25, it was observed that polymerization of the monomer virtually had not modified the size of the initial particles.

absence of double distribution of particles, which means that, during the polymerization, a second population of particles, in addition to the first population, was not created.

The dispersion obtained was an aqueous dispersion of a hybrid polymer whose particles resulted from the radical polymerization of a methyl methacrylate monomer on and/or in the particles of a preexisting polyurethane polymer.

EXAMPLES 2 TO 10

In a similar manner to that described in Example 1, various hybrid polymers were prepared according to the table below, starting from an aqueous dispersion of polyester-polyurethane containing carboxylic groups (solids content: 35.8%) sold under the name SANCUR 815 by Sancor.

The polymerization initiator was Trigonex 21S (0.5 ml).

The particle size and the polydispersity were measured for a dispersion having a solids content of 40%.

|  | Polyurethane dispersion | Water added | Monomer | Particle size | Polydispersity |
| --- | --- | --- | --- | --- | --- |
| Example 2 | 167.6 g | 192.4 g | 40 g of methyl methacrylate | 45 nm | 0.18 |
| Example 3 | 209.5 g | 240.7 g | 25 g of methyl methacrylate | 33 nm | 0.10 |

-continued

| | Polyurethane dispersion | Water added | Monomer | Particle size | Polydispersity |
|---|---|---|---|---|---|
| Example 4 | 209.5 g | 240.7 g | 25 g of cyclohexyl methacrylate | 36 nm | 0.15 |
| Example 5 | 209.5 g | 240.7 g | 25 g of isobornyl acrylate | 30 nm | 0.17 |
| Example 6 | 223.4 g | 256.7 g | 20 g of 2-ethylhexyl acrylate | 35 nm | 0.17 |
| Example 7 | 195.5 g | 224.6 g | 30 g of 2-ethylhexyl acrylate | 40 nm | 0.18 |
| Example 8 | 237.4 g | 272.8 g | 15 g of methyl methacrylate | 32 nm | 0.18 |
| Example 9 | 195.5 g | 224.6 g | 18 g of methyl methacrylate + 12 g of butyl acrylate | 41 nm | 0.35 |
| Example 10 | 195.5 g | 224.6 g | 15 g of methyl methacrylate + 15 g of butyl acrylate | 33 nm | 0.1 |

It was thus observed that for all these examples, a single, homogeneous population of particles was obtained, whose particle size was little modified by the polymerization.

EXAMPLE 11

(a) The film-formation properties of the polymer dispersions according to the invention were compared, at room temperature.

The following results were obtained:

the dispersions of Examples 1, 4, 6, 8, 9 and 10 allowed homogeneous and transparent films to be obtained after drying, the dispersions of Examples 3, 5 and 7 gave "pottery-like" films, i.e., films having microcracks.

(b) The viscosity, the hardness, the brightness, the polarity and the surface energy were measured for two dispersions according to the invention, containing or not containing a thickening agent and a dye.

The following results were obtained:
for the non-dyed, non-thickened dispersions

| | Viscosity | Brightness (black 60°) | Polarity | Surface energy |
|---|---|---|---|---|
| Example 1 | liquid | 89.6 | 25.7% | 42.8 mN/m |
| Example 9 | liquid | 89.9 | 19.8% | 35.8 mN/m |
| SANCUR 815 | | | 33% | 46.7 mN/m |

The films obtained with the aqueous dispersions of Examples 1 and 9, at 28% solids content, were very bright, and were slightly lower in polarity and surface energy than, but comparable with, those of the initial polyurethane dispersion. It was also observed that their water resistance was good: no delamination after 4 hours at 45° C. in an aqueous 1% solution of surfactant (teepol).

for the non-dyed, thickened dispersions

It was observed that the films obtained with an aqueous dispersion at a solids content of 28% containing 0.3% of polyurethane associative thickening agent SER AD FX 1100 (Servo) were very bright, high in hardness (117.5 for the dispersion of Example 1 and 89.1 for that of Example 9) and that their water resistance was good.

for the aqueous dispersions according to the invention (28% solids content), dyed (1.5% of pigments) and thickened with SER AD FX 1100 (Servo)

| | Thickening agent | Viscosity (mPa · s) | Brightness (black 60°) | Hardness | Polarity | Surface energy |
|---|---|---|---|---|---|---|
| Example 1 | 0.3% | 110/100 | 81.8 | 88.3 | 32.8% | 47.6 mN/m |
| | 0.56% | 1650/1330 | 83.1 | 167.9 | 33.6% | 49.1 mN/m |
| Example 9 | 0.3% | 340/250 | 81.9 | 65.8 | 46.2% | 43.7 mN/m |
| | 0.41% | 1100/1020 | 83.3 | 116.7 | 44.9% | 45.9 mN/m |

It was thus observed that the films obtained with the dispersions according to the invention, dyed and thickened, were of satisfactory brightness, had conventional surface energy and polarity values and were of suitable hardness.

Their water resistance was very good: no delamination after 4 hours at 45° C. in aqueous 1% solution of surfactant (teepol).

EXAMPLE 12

The properties of the films obtained were compared with:
two aqueous dispersions according to the invention (Examples 1 and 9) having a solids content of 40%
an aqueous dispersion of SANCUR 815 at a solids content of 35.8%
a mixture of 70% of a polyurethane aqueous dispersion SANCUR 815 (solids content 35.8%) and 30% of a methyl methacrylate/butyl acrylate acrylic copolymer (60/40), said mixture being of 55% solids content.

These films contained an associative thickening agent SER AD FX 1100 (0.3% by weight).

The following results were obtained:

|  | Thickening agent | Viscosity (mPa · s) | Brightness (black 60°) | Hardness | Polarity | Surface energy (mN/m) |
| --- | --- | --- | --- | --- | --- | --- |
| Example 1 | 0.56% | 1650/1330 | 83.1 | 167.9 | 33.6% | 49.1 |
| Example 9 | 0.41% | 1100/1020 | 83.3 | 116.7 | 44.9% | 45.9 |
| SANCUR 815 | 0.45% | 530/540 | 87.0 | 178.8 | 39.2% | 52.6 |
| mixture | 0.65% | 1460/1400 | 82.2 | 89.6 | 45.1% | 47.4 |

It was observed that the dispersions according to the invention had brightness and hardness properties which were comparable with those of the polyurethane dispersion alone.

However, the water resistance of the dispersions according to the invention was markedly superior to that of the polyurethane dispersion alone:

no delamination after 4 hours at 45° C. in an aqueous 1% solution of surfactant (teepol) whereas for the SANCUR dispersion, delamination of the film was observed after 2 hours.

Moreover, it was also observed that the dispersions according to the invention were appreciably harder than the dispersion obtained by simple mixing of the polyurethane and the acrylic.

EXAMPLE 13

251.6 g of polyurethane aqueous dispersion (solids content: 31.8%), sold under the name SANCUR 11600 by Sancor, were introduced into a reactor. Deionized water was added so as to obtain a dispersion of a solids content by weight of 16.6%.

20 g of cyclohexyl methacrylate were added dropwise, under nitrogen, and the mixture was then left to stir for 1 hour at 80° C.

0.8 ml of tert-butylperoxy-2-ethyl hexanoate (Trigonox 21S from Akzo) was added and the mixture was left to react for 8 hours, with stirring and under a nitrogen sparge, at 80° C.

The temperature of the reaction mixture was reduced to 25° C. and the dispersion was concentrated under reduced pressure until a solids content of 35% was obtained.

A dispersion was thus obtained which, after filtration on nylon cloth, had the following characteristics:

mean particle size determined by a quasi-elastic light-scattering apparatus of the type Coulter N4, from Coultronix: 28 nm polydispersity: 0.15

Given that the size of the particles in the initial polyurethane dispersion (SANCUR 11600) was 21 nm with a polydispersity of 0.15, it was observed that polymerization of the monomer virtually did not modify the size of the initial particles.

The dispersion obtained was an aqueous dispersion of a hybrid polymer whose particles resulted from the radical polymerization of a cyclohexyl methacrylate monomer on and/or in the particles of a preexisting polyurethane polymer.

EXAMPLE 14

74.93 g of polyurethane aqueous dispersion (solids content: 53.4%), sold under the name SANCUR 2255 by Sancor, were introduced into a reactor. Deionized water was added so as to obtain an aqueous dispersion at a solids content by weight of 16.6%.

10 g of methyl methacrylate were added dropwise, and the mixture was then left to stir for 1 hour at 80° C.

0.4 ml of tert-butylperoxy-2-ethyl hexanoate (Trigonox 21S from Akzo) was added and the mixture was left to react for 8 hours, with stirring and under a nitrogen sparge, at 80° C.

The temperature of the reaction mixture was reduced to 25° C. and the dispersion was concentrated under reduced pressure until a solids content of 30% was obtained.

A dispersion was thus obtained which, after filtration on nylon cloth, had the following characteristics:

mean particle size determined by a quasi-elastic light-scattering apparatus of the type Coulter N4, from Coultronix: 87 nm polydispersity: <0.1

Given that the size of the particles in the initial polyurethane dispersion (SANCUR 2255) was 87 nm with a polydispersity of less than 0.1, it was observed that polymerization of the monomer virtually did not modify the size of the initial particles.

The dispersion obtained was an aqueous dispersion of a hybrid polymer whose particles resulted from the radical polymerization of a methyl methacrylate monomer on and/or in the particles of a preexisting polyurethane polymer.

EXAMPLE 15

251.6 g of polyurethane aqueous dispersion (solids content: 31.8%), sold under the name SANCUR 11600 by Sancor, were introduced into a reactor. Deionized water was added so as to obtain a dispersion at a solids content by weight of 16.6%.

20 g of methyl methacrylate were added dropwise, under nitrogen, and the mixture was then left to stir for 1 hour at 80° C.

0.8 ml of tert-butylperoxy-2-ethyl hexanoate (Trigonox 21S from Akzo) was added and the mixture was left to react for 8 hours, with stirring and under a nitrogen sparge, at 80° C.

The temperature of the reaction mixture was reduced to 25° C. and the dispersion was concentrated under reduced pressure until a solids content of 35% was obtained.

A dispersion was thus obtained which, after filtration on nylon cloth, had the following characteristics:

mean particle size determined by a quasi-elastic light-scattering apparatus of the type Coulter N4, from Coultronix: 30 nm polydispersity: 0.20

Given that the size of the particles in the initial polyurethane dispersion (SANCUR 11600) was 21 nm with a polydispersity of 0.15, it was observed that polymerization of the monomer virtually did not modify the size of the initial particles.

The dispersion obtained was an aqueous dispersion of a hybrid polymer whose particles resulted from the radical polymerization of a methyl methacrylate monomer on and/or in the particles of a preexisting polyurethane polymer.

EXAMPLE 16

A nail varnish having the following composition was prepared:

dispersion of Example 6 (solids content 40%) 70%
associative polyurethane thickening agent SER AD FX 1100 (Servo) 0.47%
silicone-containing surfactant KF 355A (Shin Etsu) 0.5%
pigments 1.0%
propylene glycol 0.3%
water qs 100%

A nail varnish which covered easily and was of adequate hardness, brightness and water resistance was thus obtained.

EXAMPLE 17

A nail varnish having the following composition was prepared:

dispersion of Example 10 (solids content 40%) 70%
associative polyurethane thickening agent SER AD FX 1100 (Servo) 0.3%
silicone-containing surfactant KF 355A (Shin Etsu) 0.5%
pigments 1.0%
propylene glycol 0.3%
water qs 100%

A nail varnish which covered easily and was of adequate hardness, brightness and water resistance was thus obtained.

EXAMPLE 18

A nail varnish was prepared using the dispersion obtained in Example 13. The dispersion obtained in Example 13 was diluted so as to obtain a solids content of 30% by weight.

6.4 g of ethyl lactate were added and the mixture was left stirring for 24 hours at room temperature. The dispersion was then concentrated to a solids content of 40% by weight.

Ethyl lactate made it possible to promote the film-formation of the polymer particles contained in the dispersion, by lowering its glass transition temperature; the ethyl lactate evaporated after application of the composition and a film of suitable rigidity was obtained.

The nail varnish composition comprised:
above dispersion (solids content 40%) 70%
associative polyurethane thickening agent SER AD FX 1100 (Servo) 0.47%
silicone-containing surfactant KF 355A (Shin Etsu) 0.5%
pigments 1.0%
propylene glycol 0.3%
water qs 100%

A nail varnish which covered easily and was of adequate hardness, brightness and water resistance was thus obtained.

EXAMPLE 19

The dispersion comprising ethyl lactate prepared in Example 18 was diluted to a solids content of 5% by weight.

This dispersion may be employed as a blow-drying lotion and allows the hairstyle to be fixed well, it being possible for the said fixing to persist after two subsequent shampooings.

EXAMPLE 20

A blow-drying lotion was prepared using the dispersion obtained in Example 14.

The dispersion obtained in Example 14 was diluted so as to obtain a solids content of 30% by weight.

5.35 g of coalescence agent, sold under the name DOWANOL PMA by Dow Corning, were added and the mixture was left to stir for 24 hours at room temperature. The DOWANOL made it possible to promote the film-formation of the polymer particles contained in the dispersion, by lowering its glass transition temperature; it evaporated after application of the composition.

The dispersion was diluted to a solids content of 5% by weight.

This dispersion may be used as a blow-drying lotion and allows the hairstyle to be fixed well.

EXAMPLE 21

The dispersion obtained in Example 15 was diluted to a solids content of 17% by weight.

A mascara composition was prepared in the following way.

11.5 g of triethanolamine stearate, 7.0 g of beeswax, 4.1 g of carnauba wax and 11.4 g of paraffin were mixed together. The mixture was brought to 85° C. and 5.5 g of black iron oxide were added thereto.

A second mixture comprising 35 ml of water, 4.5 g of gum arabic and 0.16 g of hydroxyethylcellulose was prepared, and was heated to 85° C.

The two mixtures were combined and 21.3 g of the dispersion at a solids content of 17% were added.

A mascara which had good cosmetic properties on application to the eyelashes and hold in water was obtained.

What is claimed is:

1. A cosmetic or pharmaceutical composition, which comprises a cosmetically or pharmaceutically effective amount and a film-forming effective amount of an aqueous polymeric dispersion comprising particles composed of at least one radical monomer free-radically polymerized within, partially at the surface of, or within and partially at the surface of preexisting particles of at least one polymer chosen from polyurethanes and polyureas, wherein said cosmetic or pharmaceutical composition is in the form of a hair product, a make-up product, a care base for nails, a skin care product or a product intended for the photoprotection of skin, hair or skin and hair against ultraviolet radiation.

2. The composition of claim 1, wherein said at least one polymer of said preexisting particles is selected from an anionic, cationic, or amphoteric polyurethane, a polyester-polyurethane, a polyether-polyurethane, and a polyurea.

3. The composition of claim 1, wherein said at least one polymer of said preexisting particles is an aliphatic, cycloaliphatic or aromatic polyurethane, polyurea/urethane or polyurea copolymer, containing at least one sequence selected from a linear or branched aliphatic polyester, a cycloaliphatic polyester, an aromatic polyester, a linear or branched aliphatic polyether, a cycloaliphatic polyether, an aromatic polyether, a branched or unbranched, substituted or unsubstituted silicone-containing sequence, and at least one sequence containing fluorinated groups.

4. A cosmetic or pharmaceutical composition, which comprises a cosmetically or pharmaceutically effective amount and a film-forming effective amount of an aqueous polymeric dispersion comprising particles composed of at least one radical monomer free-radically polymerized within, partially at the surface of, or within and partially at the surface of preexisting particles of at least one polymer chosen from polyurethanes and polyureas, and wherein said at least one polymer of said preexisting particles is an aliphatic, cycloaliphatic or aromatic polyurethane, polyurea/urethane or polyurea copolymer, containing at least one branched or unbranched, substituted or unsubstituted silicone containing sequence selected from polydimethylsiloxane and polymethylphenylsiloxane.

5. The composition of claim 1, wherein the radical monomer is chosen from acrylic and methacrylic acid esters; N-substituted and N,N-substituted acrylamides and methacrylamides; vinyl esters; styrene; vinyl, acrylic and methacrylic monomers containing one or more siloxane groups; vinyl, allyl, ester ether and acrylamide and methacrylamide monomers containing at least one group selected from halogenated groups and a group capable of absorbing in at least one region selected from the UVA region and the UVB region.

6. A cosmetic or pharmaceutical composition, which comprises a cosmetically or pharmaceutically effective amount and a film-forming effective amount of an aqueous polymeric dispersion comprising particles composed of at least one radical monomer free-radically polymerized within, partially at the surface of, or within and partially at the surface of preexisting particles of at least one polymer chosen from polyurethanes and polyureas, and wherein said at least one radical monomer is a vinyl, allyl, ester ether, acrylamide, or methacrylamide monomer containing at least one group selected from chlorinated and fluorinated groups.

7. A cosmetic or pharmaceutical composition, which comprises a cosmetically or pharmaceutically effective amount and a film-forming effective amount of an aqueous polymeric dispersion comprising particles composed of at least one radical monomer free-radically polymerized within, partially at the surface of, or within and partially at the surface of preexisting particles of at least one polymer chosen from polyurethanes and polyureas, and wherein said at least one radical monomer is a vinyl, allyl, ester ether, acrylamide, or methacrylamide monomer containing at least one group capable of absorbing in at least one region selected from the UVA region and the UVB region, wherein said at least one group is a substituted or unsubstituted group selected from benzylidenecamphor and benzotriazole.

8. The composition of claim 7, wherein the benzotriazole group is 2-(2'-hydroxy-5-methacrylyloxyethylphenyl)-2-H-benzotriazole.

9. A cosmetic or pharmaceutical composition, which comprises a cosmetically or pharmaceutically effective amount and a film-forming effective amount of an aqueous polymeric dispersion comprising particles composed of at least one radical monomer free-radically polymerized within, partially at the surface of, or within and partially at the surface of preexisting particles of at least one polymer chosen from polyurethanes and polyureas, and wherein said at least one radical monomer is selected from vinyl, acrylic and methacrylic monomers containing one or more siloxane groups selected from:
   a. the monomer of formula $CH_2=C(CH_3)-C(O)-O-(CH_2)_3-Si-[O-Si(CH_3)_3]_3$ and
   b. silicone-containing macromonomers containing a vinyl, allyl, ester ether acrylamide or methacrylamide monofunctional end group of formula $CH_2=C(R1)-C(O)-X-(CH_2)_p-[Si(CH_3)(R4)-O-]_n-Si(CH_3)_2-R3$, in which R1 represents H or $CH_3$, X represents O or NH, p is an integer which may be zero, R3 and R4 independently represent an aliphatic, cycloaliphatic or aromatic group, and n is an integer.

10. A composition according to claim 1, wherein said composition is in the form of an aerosol fixing hairspray, a shampoo, a styling lotion, a styling mousse, a mascara, a nail varnish, a care base for nails, or a product intended for the photoprotection of skin, hair, or skin and hair against ultraviolet radiation.

11. The composition of claim 1, wherein the aqueous polymeric dispersion further contains a thickening agent or a dye.

12. A method of forming a film in a cosmetic or pharmaceutical composition, comprising the step of forming a film in said cosmetic or pharmaceutical composition by using an aqueous polymeric dispersion comprising particles composed of at least one radical monomer free-radically polymerized within, partially at the surface of, or within and partially at the surface of preexisting particles of at least one polymer chosen from polyurethanes and polyureas, wherein said aqueous polymeric dispersion is present in an amount effective for forming a film in said cosmetic or pharmaceutical composition, and further wherein said cosmetic or pharmaceutical composition is in the form of a hair product, a make-up product, a care base for nails, a skin care product or a product intended for the photoprotection of skin, hair or skin and hair against ultraviolet radiation.

13. The method of claim 12, wherein said at least one polymer of said preexisting particles is an aliphatic, cycloaliphatic or aromatic polyurethane, polyurea/urethane or polyurea copolymer, containing at least one sequence selected from a linear or branched aliphatic polyester, a cycloaliphatic polyester, an aromatic polyester, an aliphatic polyether, a cycloaliphatic polyether, an aromatic polyether, a branched or unbranched, substituted or unsubstituted silicone-containing sequence, and at least one sequence containing fluorinated groups.

14. A method of forming a film in a cosmetic or pharmaceutical composition, comprising the step of forming a film in said cosmetic or pharmaceutical composition by using an aqueous polymeric dispersion comprising particles composed of at least one radical monomer free-radically polymerized within, partially at the surface of, or within and partially at the surface of preexisting particles of at least one polymer chosen from polyurethanes and polyureas, wherein said aqueous polymeric dispersion is present in an amount effective for forming a film in said cosmetic or pharmaceutical composition, and wherein said at least one polymer of said preexisting particles is an aliphatic, cycloaliphatic or aromatic polyurethane, polyurea/urethane or polyurea copolymer, containing at least one branched or unbranched, substituted or unsubstituted silicone containing sequence selected from polydimethylsiloxane and polymethylphenylsiloxane.

15. The method of claim 12, wherein the radical monomer is chosen from acrylic and methacrylic acid esters; N-substituted and N,N-substituted acrylamides and methacrylamides; vinyl esters; styrene; vinyl, acrylic and methacrylic monomers containing one or more siloxane groups; vinyl, allyl, ester ether and acrylamide and methacrylamide monomers containing at least one group selected from halogenated groups and a group capable of absorbing in at least one region selected from the UVA region and the UVB region.

16. A method of forming a film in a cosmetic or pharmaceutical composition, comprising the step of forming a film in said cosmetic or pharmaceutical composition by using an aqueous polymeric dispersion comprising particles composed of at least one radical monomer free-radically polymerized within, partially at the surface of, or within and partially at the surface of preexisting particles of at least one polymer chosen from polyurethanes and polyureas, wherein said aqueous polymeric dispersion is present in an amount effective for forming a film in said cosmetic or pharmaceutical composition, and wherein said at least one radical monomer is a vinyl, allyl, ester ether, acrylamide, or methacrylamide monomer containing at least one group selected from chlorinated and fluorinated groups.

17. A method of forming a film in a cosmetic or pharmaceutical composition, comprising the step of forming a film in said cosmetic or pharmaceutical composition by using an aqueous polymeric dispersion comprising particles composed of at least one radical monomer free-radically polymerized within, partially at the surface of, or within and partially at the surface of preexisting particles of at least one polymer chosen from polyurethanes and polyureas, wherein said aqueous polymeric dispersion is present in an amount effective for forming a film in said cosmetic or pharmaceutical composition, and wherein said at least one radical monomer is a vinyl, allyl, ester ether, acrylamide, or methacrylamide monomer containing at least one group capable of absorbing in at least one region selected from the UVA region and the UVB region, wherein said at least one group is a substituted or unsubstituted group selected from benzylidenecamphor and benzotriazole.

18. A method of forming a film in a cosmetic or pharmaceutical composition, comprising the step of forming a film in said cosmetic or pharmaceutical composition by using an aqueous polymeric dispersion comprising particles composed of at least one radical monomer free-radically polymerized within, partially at the surface of, or within and partially at the surface of preexisting particles of at least one polymer chosen from polyurethanes and polyureas, wherein said aqueous polymeric dispersion is present in an amount effective for forming a film in said cosmetic or pharmaceutical composition, and wherein said at least one radical monomer is selected from vinyl, acrylic and methacrylic monomers containing one or more siloxane groups selected from:

a. the monomer of formula $CH_2=C(CH_3)-C(O)-O-(CH_2)_3-Si-[O-Si(CH_3)_3]_3$ and
  b. silicone-containing macromonomers containing a vinyl, allyl, ester ether acrylamide or methacrylamide monofunctional end group of formula $CH_2=C(R1)-C(O)-X-(CH_2)_p-[Si(CH_3)(R4)-O-]_n-Si(CH_3)_2-R3$, in which R1 represents H or $CH_3$, X represents O or NH, p is an integer which is optionally zero, R3 and R4 independently represent an aliphatic, cycloaliphatic or aromatic group, and n is an integer.

19. The method of claim 12, wherein the cosmetic composition is a product intended for the photoprotection of skin, hair, or skin and hair against ultraviolet radiation, an aerosol fixing hairspray, a shampoo, a styling lotion or a styling mousse, a nail varnish, a mascara, a care base for nails, or a skin care product.

20. The composition of claim 1, wherein the radical monomer is present in an amount ranging from about 10–95% by weight, and the polymer of said preexisting particles is present in an amount ranging from about 5–90% by weight.

21. The method of claim 12, wherein the radical monomer is present in an amount ranging from about 10–95% by weight, and the polymer of said preexisting particles is present in an amount ranging from about 5–90% by weight.

22. The composition of claim 9, wherein said aliphatic group of $R_3$ and $R_4$ is $CH_3$.

23. The method of claim 18, wherein said aliphatic group of $R_3$ and $R_4$ is $CH_3$.

* * * * *